(12) United States Patent
Lee et al.

(10) Patent No.: US 6,235,447 B1
(45) Date of Patent: May 22, 2001

(54) PHOTORESIST MONOMERS, POLYMERS THEREOF, AND PHOTORESIST COMPOSITIONS CONTAINING THE SAME

(75) Inventors: Geun Su Lee; Cha Won Koh; Jae Chang Jung; Min Ho Jung; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/418,724

(22) Filed: Oct. 15, 1999

(30) Foreign Application Priority Data

Oct. 17, 1998 (KR) ................................. 98/043431
Feb. 4, 1999 (JP) .................................... 99/03650

(51) Int. Cl.[7] ................................... G03F 7/004
(52) U.S. Cl. ...................... 430/270.1; 430/326; 526/281; 526/271; 562/498
(58) Field of Search ................ 430/270.1, 326; 526/281, 271; 562/498

(56) References Cited

U.S. PATENT DOCUMENTS

| | | | |
|---|---|---|---|
| 5,843,624 | * 12/1998 | Houlihan et al. | 430/296 |
| 6,048,664 | * 4/2000 | Houlihan et al. | 430/270.1 |
| 6,063,542 | * 5/2000 | Hyeon et al. | 430/270.1 |
| 6,136,499 | * 10/2000 | Goodall et al. | 430/270.1 |
| 6,143,466 | * 11/2000 | Choi | 430/270.1 |

FOREIGN PATENT DOCUMENTS

2332679 * 6/1999 (GB) .

* cited by examiner

*Primary Examiner*—Cynthia Hamilton
*Assistant Examiner*—Rosemary Ashton
(74) *Attorney, Agent, or Firm*—Townsend and Townsend and Crew LLP

(57) ABSTRACT

The present invention relates to novel monomers which can be used to form photoresist polymers and photoresist compositions using the same which are suitable for photolithography processes employing a far ultraviolet light source, copolymers thereof. Preferred monomers of the invention are represented by Chemical Formula 1 below:

<Chemical Formula 1>

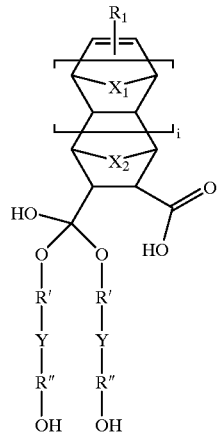

wherein, $X_1$ and $X_2$ individually represent $CH_2$, $CH_2CH_2$, oxygen or sulfur; Y represents $CH_2$ or oxygen; $R_1$ represents H or $CH_3$, R' and R" individually represent substituted or non-substituted ($C_0$–$C_3$) alkyl; and i represents an integer from 0 to 3.

35 Claims, No Drawings

PHOTORESIST MONOMERS, POLYMERS THEREOF, AND PHOTORESIST COMPOSITIONS CONTAINING THE SAME

FIELD OF THE INVENTION

The present invention relates to photoresist monomers, polymers formed therefrom, and photoresist compositions containing same, more specifically, photoresist monomers, polymers and a photoresist compositions suitable for photolithography processes employing DUV (deep ultraviolet) light sources such as KrF (249 mm) and ArF(193 um); EUV; VUV; E-beam; ion-beam; and X-ray.

BACKGROUND OF THE INVENTION

Recently, chemical amplification type DUV photoresists have been investigated in order to achieve high sensitivity in minute image formation processes for preparing semiconductor devices. Such photoresists are prepared by blending a photoacid generator and matrix resin polymer having an acid labile group.

According to the reaction mechanism of such a photoresist, the photoacid generator generates acid when it is illuminated by a light source, and the main chain or branched chain of the resin is reacted with the generated acid to be decomposed or crosslinked. The polarity change of the resin induces solubility differences between the exposed portion and unexposed portion in the developing solution, to form a predetermined pattern.

In the lithography process, resolution depends upon the wavelength of the light source—the shorter the wavelength, the more minute pattern can be formed.

In general, a photoresist (hereinafter, abbreviated to as "PR") must satisfy various requisites such as excellent etching resistance, heat resistance and adhesiveness, and more preferably, it should be developable in 2.38% aqueous tetramethylammonium hydroxide (TMAH) solution. However, it is very difficult to synthesize a polymer that satisfies all of these requisites. For example, a polymer having a polyacrylate main chain can be easily synthesized, but it has poor etching resistance and has difficulties in the developing process. In order to secure etching resistance, it has been considered to add an alicyclic unit to the main chain. However, in this case, it is very difficult to form a copolymer wherein the main chain is comprised entirely of alicyclic units.

As an attempt to solve the problems described above, Bell Research Center developed a polymer having the following chemical structure, wherein the main chain is substituted with norbornene, acrylate and maleic anhydride units.

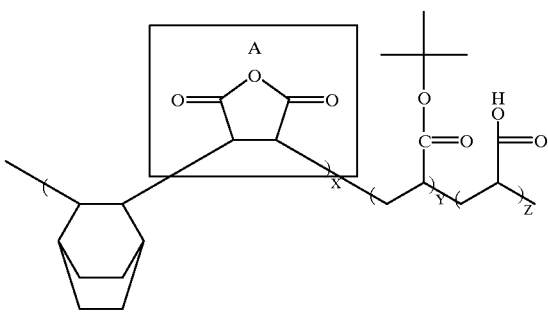

However, the above polymer has a problem in that the maleic anhydride moiety ('A' portion), which is employed to polymerize alicyclic olefin groups, is readily dissolved in 2.38 wt % aqueous TMAH solution even in an unexposed condition. Thus, in order to inhibit the dissolution of the polymer in the unexposed section, the ratio of 'Y' portion having tert-butyl substituent should be increased, but this results in a relative decrease of the 'Z' portion (which has a role of increasing adhesiveness to the substrate), and therefore the PR might be easily separated from the substrate at the time of patterning.

In order to solve the problem, cholesterol type dissolution inhibitors have been added to the polymer to form a two-component system. However, since the amount of the dissolution inhibitor is very high [about 30% (w/w) of the resin], reappearance is low and the production cost is high, thereby making the system unsuitable as a PR.

SUMMARY OF THE INVENTION

An object of the present invention is to provide novel PR monomers that can form polymers having excellent etching resistance, adhesiveness and photosensitivity, and can be manufactured on a large scale at a low production cost, and a process for preparing the monomers.

Another object of the present invention is to provide PR polymers having excellent etching resistance, adhesiveness and photosensitivity, and a process for preparing the same.

Another object of the present invention is to provide photoresist compositions using the PR polymers described above, and a process for preparing the same.

Still another object of the present invention is to provide a semiconductor element produced by using the photoresist composition.

In order to achieve these objects, the present invention provides a monomer represented by following Chemical Formula 1:

<Chemical Formula 1>

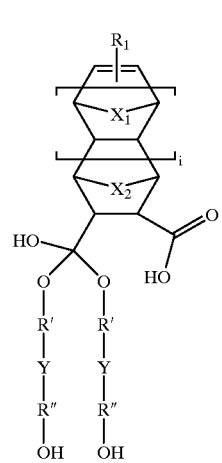

wherein, $X_1$ and $X_2$ individually represent $CH_2$, $CH_2CH_2$, oxygen or sulfur; Y represents $CH_2$ or oxygen; $R_1$ represents H or $CH_3$, R' and R" individually represent substituted or non-substituted ($C_0$–$C_3$) alkyl, and i is an integer from 0 to 3.

In order to achieve other technical objects, copolymers are provided comprising said monomer of Chemical Formula 1. The most preferred copolymers are represented by the following Chemical Formula 6:

Chemical Formula 6

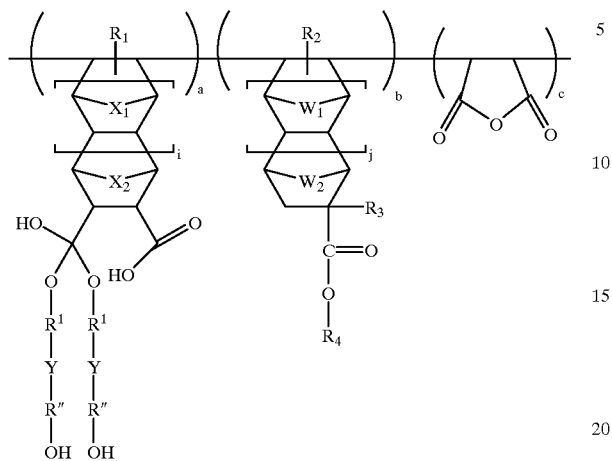

<Chemical Formula 1>

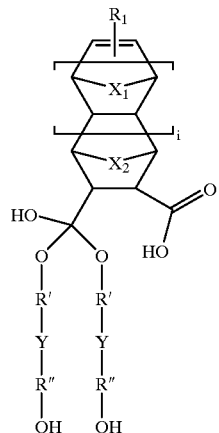

wherein, $X_1$ and $X_2$ individually represent $CH_2$, $CH_2CH_2$, oxygen or sulfur; Y represents $CH_2$ or oxygen; $R_1$ represents H or $CH_3$, R' and R" individually represent substituted or non-substituted($C_0$–$C_3$)alkyl and i is an integer from 0 to 3.

The compound of Chemical Formula 1 provides several advantages as a monomer in a photoresist polymer:
1) it provides excellent adhesiveness to the substrate, as it has three hydroxyl groups per mole;
2) since it also has a carboxyl group, it provides excellent photosensitivity;
3) it does not have an offensive odor; and
4) it can be manufactured on a large scale at a low production cost, because it can be simply synthesized by recrystallization, without complicated separating means such as distillation or column chromatography.

The novel monomer (Chemical Formula 1) according to the present invention can be prepared by (1) dissolving in an organic reaction solvent, a compound of Chemical Formula 2:

<Chemical Formula 2>

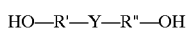

HO—R'—Y—R"—OH wherein Y represents $CH_2$ or oxygen; R' and R" individually represent substituted or non-substituted ($C_0$–$C_3$) alkyl;
(2) reacting therewith in the presence of an acid catalyst, or under basic conditions, a compound of Chemical Formula 3:

Chemical 3

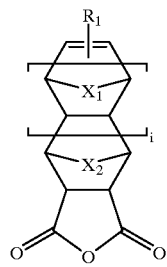

wherein $X_1$ and $X_2$ individually represent $CH_2$, $CH_2CH_2$, oxygen or sulfur; Y represents $CH_2$ or oxygen; $W_1$ and $W_2$ individually represent $CH_2$, $CH_2CH_2$ or oxygen; $R_1$, $R_2$ and $R_3$ individually represent H or $CH_3$; $R_4$ represents an acid labile protective group; R' and R" individually represent substituted or non-substituted ($C_0$–$C_3$) alkyl; i and j individually represent integers from 0 to 3; and a, b, c and d represent the number of repeating units derived from each monomer.

In addition, a novel photoresist composition is provided comprising the copolymer as described above, a photoacid generator and a conventional organic solvent.

DETAILED DESCRIPTION OF THE INVENTION

Synthesis of Novel Photoresist Monomers

The present inventors have found that a bicyclic derivative containing a hydroxyl group enhances adhesiveness and that a bicyclic derivative containing carboxylic group(s) contributes enhancement of photosensitivity in a photoresist resin (also referred to herein as a copolymer), and have prepared novel monomers of following Chemical Formula 1:

wherein $X_1$ and $X_2$ individually represent $CH_2$, $CH_2CH_2$, oxygen or sulfur; $R_1$ represents H or $CH_3$, and i is an integer from 0 to 3.

(3) distilling off the organic reaction solvent and neutralizing the resulting residue;

(4) extracting the organic layer from the neutralized residue and distilling off the organic solvent; and (5) crystallizing the monomer from the resultant residue in an organic crystallization solvent such as benzene.

The compound of Chemical Formula 2 is preferably used in an amount equal to 2 molar equivalents or more. The compounds represented by Chemical Formula 2 include ethylene glycol, 1,3-propanediol, 1,4-butanediol, 1,5-pentanediol and diethylene glycol; and the compounds represented by Chemical Formula 3 include 5-norbornene-2,3-dicarboxylic anhydride, methyl-5-norbornene-2,3-dicarboxylic anhydride and exo-3,6-epoxy-1,2,3,6-tetrahydrophthalic anhydride. As the organic solvent, tetrahydrofuran, dimethylformamide, dioxane, benzene, toluene, or the like may be used.

Since the novel monomers synthesized according to the present invention have both hydroxyl group(s) and carboxylic group, PR copolymers including said monomer show excellent adhesiveness and sensitivity. In addition, the novel monomers according to the present invention can be simply synthesized. In other words, pure monomers can be obtained by recrystallization. Thus, complicated separating means such as distillation or column chromatography is not necessary, thereby allowing the monomers to be produced on a large scale at a low cost.

In the embodiments of the present invention which will be described below (Examples 1 to 15), sodium hydride (NaH) was used as the reaction catalyst, but other basic catalysts such as KH, $CaH_2$, $Na_2CO_3$, $K_2CO_3$, LDA (lithium diisopropylamide), or the like may be used. Instead of using a basic catalyst, the reaction may also be performed in the presence of an acid catalyst such as sulfuric acid, acetic acid or nitric acid. In these Examples, hydrochloric acid was used as a neutralizing agent, however, any conventional acid such as nitric acid, sulfuric acid or acetic acid may be used. When an acid catalyst is used, a base is used as a neutralizing agent.

Preparation of the Photoresist Polymers

The present inventors have synthesized photoresist copolymers comprising the monomer of Chemical Formula 1.

In order to further enhance photosensitivity of the photoresist resin, it is preferable to copolymerize the monomer of Chemical Formula 1 with a compound of Chemical Formula 4 having an acid labile protective group as a second monomer:

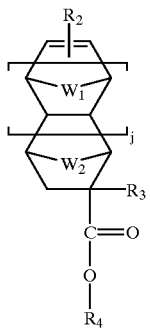

Chemical Formula 4 wherein $W_1$ and $W_2$ individually represent $CH_2$, $CH_2CH_2$ or oxygen; $R_2$ and $R_3$ individually represent H or $CH_3$; $R_4$ is an acid labile protective group; and j is an integer from 0 to 3.

The acid labile protective group can be any of the known protective groups that can be substituted by an acid and functions to prevent the compound to which the group is bound from dissolving in the alkaline developer solution. Preferable acid labile protective groups are selected from the group consisting of tert-butyl, 2-tetrahydrofuranyl and 2-tetrahydropyranyl.

It is possible to perform the polymerization of the copolymers of the present invention only with alicyclic olefin monomers when a metal catalyst such as platinum or nickel is employed in the polymerization process. In such case, the copolymer may comprise only repeating units of the monomer of Chemical Formula 1 and the monomer of Chemical Formula 4. However, it is preferable to perform the polymerization without using such special catalyst by employing maleic anhydride as a third monomer. The amount of maleic anhydride is preferably identical to that of the alicyclic olefin compounds employed in the copolymerization so that in the resultant polymer a repeating unit of maleic anhydride is after a repeating unit of each alicyclic olefin monomer. In other words, maleic anhydride is preferably present in an amount equal to 50% of the total amount of monomers used.

Furthermore, since the compound of Chemical Formula 1 has two sterically bulky substituents, a hydrophilic group and a carboxylic group, it has been found that the addition of a fourth monomer having little steric hindrance (a "spacer monomer") makes it possible to properly control the molecular weight of the copolymer to about 7000 to 8000 and to increase the polymerization yield to about 40% or more. Preferred spacer monomers have the following Chemical Formula 5:

Chemical Formula 5 wherein, Z represents $CH_2$, $CH_2CH_2$ or oxygen.

Further, the present inventors have found that the above spacer monomer not only enhances the yield, but also has the effect of decreasing the etching rate, when compared with conventional photoresist resins used with deep ultraviolet light sources. In cases in which chlorine gas is used as an etching gas, the etching rate of a photoresist resin comprising a spacer monomer of the present invention (norbornene) was about 0.85 to 0.92, whereas the etching rate of a conventional photoresist suitable for use with a deep ultraviolet light source which does not contain a spacer monomer is about 1.0.

The most preferred photoresist copolymers according to the present invention are represented by following Chemical Formula 6:

<Chemical Formula 6>

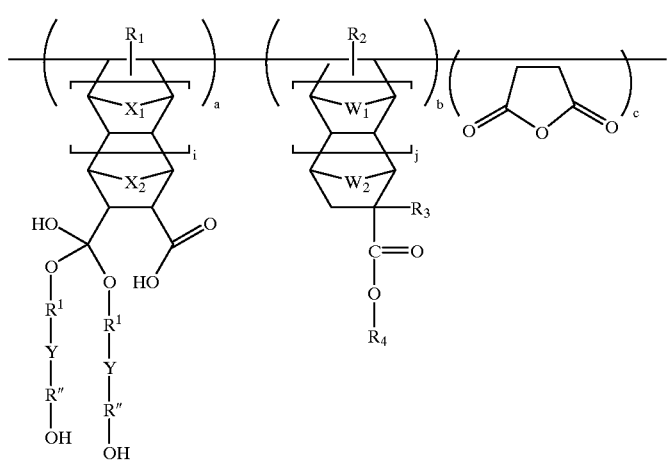

wherein $X_1$ and $X_2$ individually represent $CH_2$, $CH_2CH_2$, oxygen or sulfur; Y represents $CH_2$ or oxygen; $W_1$ and $W_2$ individually represent $CH_2$, $CH_2CH_2$ or oxygen; $R_1$, $R_2$ and $R_3$ individually represent H or $CH_3$; $R_4$ represents an acid labile protective group; R' and R" individually represent substituted or non-substituted ($C_0$–$C_3$)alkyl; i and j individually represent integers from 0 to 3; and a, b, c and d represent the number of repeating units derived from each monomer.

Preferably, molecular weights of the copolymer represented by Chemical Formula 6 are from 3,000 to 100,000, most preferably 5,000 to 8,000. The ratio, a:b:c:d is preferably 1–20 mol %: 10–40 mol % : 50 mol %: 1–30%. The most preferred copolymers comprise a maleic anhydride unit after each alicyclic monomer unit.

The compound of Chemical Formula 6 can be synthesized by dissolving in a conventional organic solvent (i) the compound of Chemical Formula 1 (the first monomer), (ii) a compound of Chemical Formula 4 (the second monomer), (iii) maleic anhydride (the third monomer) and (iv) a spacer monomer, preferably a norbornene derivative (the fourth monomer), and adding a conventional radical polymerization initiator thereto to carry out the copolymerization.

As the polymerization solvent, tetrahydrofuran, dimethylformamide, dimethyl sulfoxide, dioxane, cyclohexanone, methyl ethyl ketone, benzene, toluene or xylene may be used. As the polymerization initiator, conventional radical polymerization initiators such as 2,2-azobisisobutyronitile (AIBN), acetyl peroxide, lauryl peroxide, benzoyl peroxide, tert-butyl peroxide and tert-butyl peracetate may be used.

Preparation of Photoresist Compositions, and Formation of a Photoresist Pattern by using the Same A photoresist composition usable with light sources in the deep ultraviolet region of the spectrum, in particular, an ArF light source, was prepared by dissolving a copolymer of the present invention in a conventional organic solvent containing a conventional photoacid generator.

As the photoacid generator, sulfide or onium type compounds are preferably used. Suitable photoacid generator may be one or more compounds selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate. The photoacid generator is used in an amount of 0.05 to 10% by weight of the photoresist resin employed. If the amount of the photoacid generator is less than 0.05% by weight, photosensitivity of the photoresist is poor. On the other hand, if the amount is more than 10%, the photoacid generator readily absorbs deep ultraviolet to provide a pattern having poor cross-sectional surface.

As examples of a conventional organic solvent, ethyl 3-ethoxypriopionate, methyl 3-methoxypropionate, cyclohexanone, cyclopentanone, propylene glycol methyl ether acetate, or the like may be used. The amount of solvent used is preferably 200 to 1000% by weight of the photoresist resin employed, in order to obtain a photoresist layer of desirable thickness when coated on a suitable substrate such as a silicon wafer to form a semiconductor element. According to experiments performed by the inventors, when the amount of solvent is 600% by weight, a photoresist layer having 0.5 µm of thickness may be obtained.

A photoresist pattern formed on a semiconductor element employing a photoresist composition according to the present invention showed excellent adhesiveness without being broken, even with L/S (line/space) patterns of 60 nm or less.

According to the present invention, a photoresist composition having excellent etching resistance and adhesiveness can be produced on a large scale at low production cost, thereby producing a highly reliable semiconductor element.

The invention is described in more detail by referring to the examples below, but it should be noted that the present invention is not restricted to these examples.

EXAMPLE 1

Synthesis of 5-norbornene-2-carboxylic acid-3-[1,1-di(2-hydroxyethoxy)]methanol

Ethylene glycol (0.22 mole) was added to 100 ml of tetrahydrofuran, and the mixture was chilled to −20° C. After chilling, 0.2 mole of NaH was added to establish a basic condition, and the resultant mixture was stirred for 20–30 minutes. Then, 5-norbornene-2,3-dicarboxylic anhydride (0.1 mole) was slowly added as a starting material, and the temperature was raised to ambient temperature to perform the reaction for 24 hours. When the reaction was completed, tetrahydrofuran was distilled off, and 0.2N HCl solution (1 liter) was added to the residue to neutralize the solution. Then, the neutralized solution was extracted with ethyl acetate, and the extracted organic layer was dried, and distilled to remove ethyl acetate, and the residue was crystallized from benzene. The resultant residue was filtered off and dried to obtain the compound 5-norbornene-2-carboxylic acid-3-[1,1-di(2-hydroxyethoxy)]methanol represented by Chemical Formula 7 as a pure colorless solid (yield: 91%).

<Chemical Formula 7>

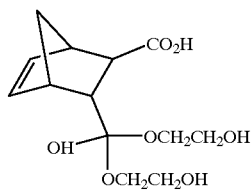

EXAMPLE 2

Synthesis of 5-norbornene-2-carboxylic acid-3-[1,1-di(3-hydroxypropyloxy)]methanol The procedure of Example 1 was repeated but using 1,3-propanediol instead of ethylene glycol as a starting material, to obtain 5-norbornene-2-carboxylic acid-3-[1,1-di(3-hydroxypropyloxy)methanol, the compound of Chemical Formula 8 as colorless solid (21.1 g/yield: 88%).

<Chemical Formula 8>

EXAMPLE 3

Synthesis of 5-norbornene-2-carboxylic acid-3-[1,1-di(4-hydroxybutyloxy)]methanol The procedure of Example 1 was repeated but using 1,4-butanediol instead -of ethylene glycol as a starting material, to obtain 5-norbornene-2-carboxylic acid-3-[1,1-di(4-hydroxybutyloxy)]methanol, the compound of Chemical Formula 9 as a colorless solid (22.6 g/yield: 89%).

<Chemical Formula 9>

EXAMPLE 4

Synthesis of 5-norbornene-2-carboxylic acid-3-[1,1-di(5-hydroxypentyloxy)]methanol The procedure of Example 1 was repeated but using 1,5-pentanediol instead of ethylene glycol as a starting material, to obtain 5-norbornene-2-carboxylic acid-3-[1,1-di(5-hydroxypentyloxy)]methanol, the compound of Chemical Formula 10 as colorless solid (22.8 g/yield: 85%).

<Chemical Formula 10>

EXAMPLE 5

Synthesis of 5-norbornene-2-carboxylic acid-3-[1,1-di(2-hydroxyethoxyethoxy)]methanol The procedure of Example 1 was repeated but using diethylene glycol instead of ethylene glycol as a starting material, to obtain 5-norbornene-2-carboxylic acid-3-[1,1-di(2-hydroxyethoxyethoxy)]methanol, the compound of Chemical Formula 11 as a colorless solid (19.2 g/yield: 71%).

<Chemical Formula 11>

EXAMPLE 6

Synthesis of methyl 5-norbornene-2-carboxylic acid-3-[1,1-di(2-hydroxyethoxy)]methanol The procedure of Example 1 was repeated but using methyl-5-norbornene-2,3-dicarboxylic anhydride instead of 5-norbornene-2,3-dicarboxylic anhydride as a reactant, to obtain methyl 5-norbornene-2-carboxylic acid-3-[1,1-di(2-hydroxyethoxy)]methanol, the compound of Chemical Formula 12 as a colorless solid (22.8 g/yield: 85%).

<Chemical Formula 12>

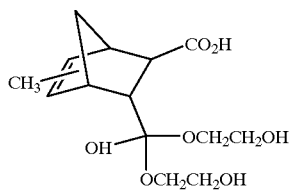

EXAMPLE 7

Synthesis of methyl 5-norbornene-2-carboxylic acid-3-[1,1-di(3-hydroxypropyloxy)]methanol The procedure of Example 2 was repeated but using methyl-5-norbornene- 2,3-dicarboxylic anhydride instead of 5-norbornene-2,3-dicarboxylic anhydride as a reactant, to obtain methyl 5-norbornene-2-carboxylic acid-3-[1,1-di(3-hydroxypropyloxy)]methanol, the compound of following Chemical Formula 13:

<Chemical Formula 13>

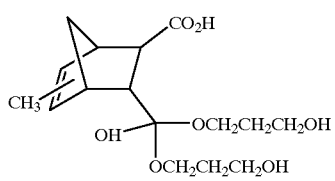

EXAMPLE 8

Synthesis of methyl 5-norbornene-2-carboxylic acid-3-[1,1-di(4-hydroxybutyloxy)]methanol The procedure of Example 3 was repeated but using methyl-5-norbornene-2,3-dicarboxylic anhydride instead of 5-norbornene-2,3-dicarboxylic anhydride as a reactant, to obtain methyl 5-norbornene-2-carboxylic acid-3-[1,1-di(4-hydroxybutyloxy)]methanol, the compound of following Chemical Formula 14:

<Chemical Formula 14>

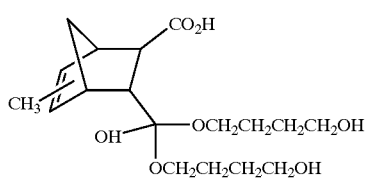

EXAMPLE 9

Synthesis of methyl 5-norbornene-2-carboxylic acid-3-[1,1-di(5-hydroxypentyloxy)]methanol The procedure of Example 4 was repeated but using methyl-5-norbornene-2,3-dicarboxylic anhydride instead of 5-norbornene-2,3-dicarboxylic anhydride as a reactant, to obtain the compound of following Chemical Formula 15:

<Chemical Formula 15>

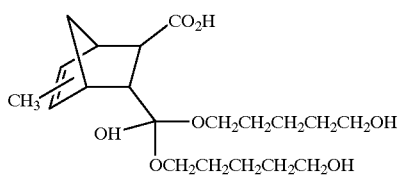

EXAMPLE 10

Synthesis of methyl 5-norbornene-2-carboxylic acid-3-[1,1-di(2-hydroxyethoxyethoxy)]methanol The procedure of Example 5 was repeated but using methyl-5-norbornene-2,3-dicarboxylic anhydride instead of 5-norbornene-2,3-dicarboxylic anhydride as a reactant, to obtain the compound of following Chemical Formula 16:

<Chemical Formula 16>

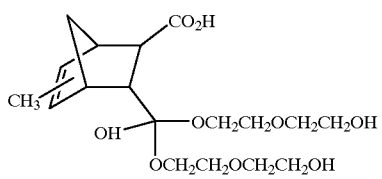

EXAMPLE 11

Synthesis of oxabicyclo[2.2.1]hept-5-ene-2-carboxylic acid-3-[1,1-di(2-hydroxyethoxy)]methanol Ethylene glycol (0.22 mole) was added to 100 ml of tetrahydrofuran as a starting material, and the mixture was chilled to −20° C. To the chilled mixture, sodium hydride (0.2 mole) was added to establish a basic condition, and the resultant mixture was stirred for 20–30 minutes. Then, 0.1 mole of exo-3,6-epoxy-1,2,3,6-tetrahydrophthalic anhydride was slowly added thereto as a reactant, and the temperature was raised to room temperature to perform the reaction for 24 hours. When the reaction was completed, tetrahydrofuran was distilled off. Then, 0.2 N hydrochloric acid solution (1 liter) was added to the residual solution to neutralize the solution, and the ethyl acetate layer was dried with magnesium sulfate and evaporated to remove the solvent. The residue was crystallized from benzene. The resultant residue was filtered off and dried to obtain oxabicyclo[2.2.1]hept-5-ene-2-carboxylic acid-3-[1,1-di(2-hydroxyethoxy)]methanol, the compound of Chemical Formula 17, as a pure colorless solid (yield: 91%).

<Chemical Formula 17>

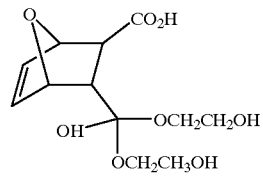

EXAMPLE 12

Synthesis of oxabicyclo[2.2.1]hept-5-ene-2-carboxylic acid-3-1,1-di(3-hydroxypropyloxy)methanol The procedure of Example 11 was repeated but using 1,3-propanediol instead of ethylene glycol as a starting material, to obtain oxabicyclo[2.2.1]-hept-5-ene-2-carboxylic acid-3-[1,1-di(3-hydroxypropyloxy)]methanol, the compound of Chemical Formula 18 as a colorless solid (20.8 g/yield: 86%).

<Chemical Formula 18>

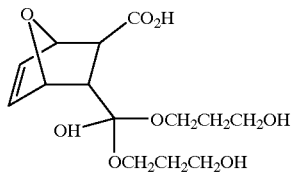

Example 13

Synthesis of oxabicyclo[2.2.1]hept-5-ene-2-carboxylic acid-3-1,1-di(4-hydroxybutyloxy)methanol The procedure of Example 11 was repeated but using 1,4-butanediol instead of ethylene glycol as a starting material, to obtain oxabicyclo[2.2.1]-hept-5-ene-2-carboxylic acid-3-[1,1-di(4-hydroxybutyloxy)]methanol, the compound represented by Chemical Formula 19 as a colorless solid (22.3 g/yield: 87%).

<Chemical Formula 19>

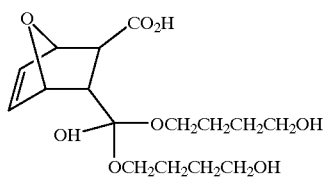

EXAMPLE 14

Synthesis of oxabicyclo[2.2.1]hept-5-ene-2-carboxylic acid-3-[1,1-di(5-hydroxyethoxyethoxy)]methanol The procedure of Example 11 was repeated but using 1,5-pentanediol instead of ethylene glycol as a starting material, to obtain oxabicyclo[2.2.1]-hept-5-ene-2-carboxylic acid-3-[1,1-di(5-hydroxypentyloxy)]methanol, the compound represented by Chemical Formula 20 as a colorless solid (23.8 g/yield: 88%).

<Chemical Formula 20>

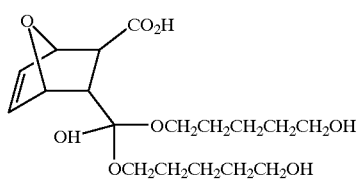

EXAMPLE 15

Synthesis of oxabicyclo[2.2.1]hept-5-ene-2-carboxylic acid-3-[1,1-di(2-hydroxyethoxyethoxy)]methanol The procedure of Example 11 was repeated but using diethylene glycol instead of ethylene glycol as a starting material, to obtain oxabicyclo[2.2.1]-hept-5-ene-2-carboxylic acid-3-[1,1-di(2-hydroxyethoxyethoxy)]methanol, the compound represented by Chemical Formula 21 as a colorless solid (21.2 g/yield: 78%).

Chemical Formula 21

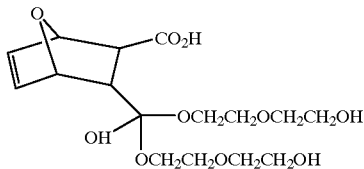

EXAMPLE 16

Synthesis of poly(5-norbornene-2-carboxylic acid-3-[1,1-di(2-hydroxyethoxy)]methanol/maleic anhydride/norbornene/tert-butyl-5-norbornene-2-carboxylate)

In 25 ml of tetrahydrofuran, 5-norbornene-2-carboxylic acid-3-[1,1-di(2-hydroxyethoxy)]methanol (10 mmol), maleic anhydride (100 mmol), norbornene (20 mmol), tert-butyl-5-norbornene-2-carboxylate (70 mmol) and AIBN (0.30 g) were dissolved, and the solution was reacted at 65° C. for 10 hours. When the reaction was completed, the reaction mixture was poured into petroleum ether, to obtain a pure solid, which was then filtered and dried to give the compound of Chemical Formula 22 (11.3 g/yield: 42%).

Chemical Formula 22

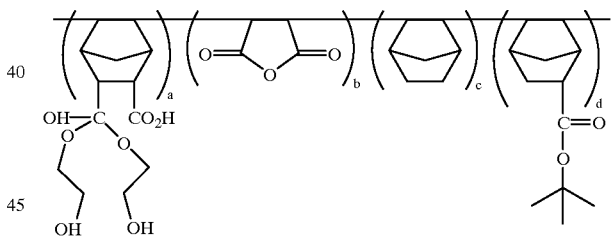

In the Example, petroleum ether was used as a crystallization solvent, but diethyl ether, methanol, ethanol or isopropanol may also be employed as the crystallization solvent instead of petroleum ether.

EXAMPLE 17

Synthesis of poly(5-norbornene-2-carboxylic acid-3-[1,1-di(3-hydroxypropyloxy)]methanol/maleic anhydride/norbornene/tert-butyl-5-norbornene-2-carboxylate)

The procedure of Example 16 was repeated but using 5-norbornene-2-carboxylic acid-3-[1,1-di(3-hydroxypropyloxy)]methanol instead of 5-norbornene-2-carboxylic acid-3-[1,1-di(2-hydroxyethoxy)methanol to obtain the compound represented by following Chemical Formula 23 as a colorless solid (11.58 g/yield: 41%).

Chemical Formula 23

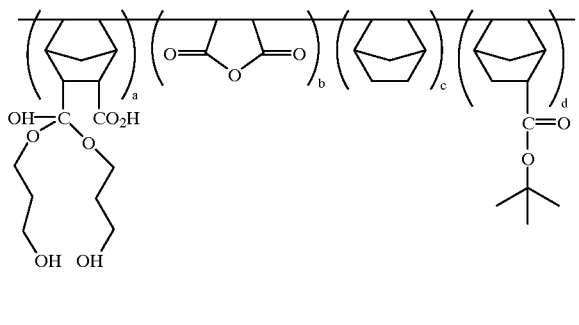

EXAMPLE 18

Synthesis of poly(5-norbornene-2-carboxylic acid-3-[1,1-di(4-hydroxybutyloxy)]methanol/maleic anhydride/norbornene/tert-butyl-5-norbornene-2-carboxylate)

The procedure of Example 16 was repeated but using 5-norbornene-2-carboxylic acid-3-[1,1-di(4-hydroxybutyloxy)]methanol instead of 5-norbornene-2-carboxylic acid-3-[1,1-di(2-hydroxyethoxy)]methanol, to obtain the compound represented by following Chemical Formula 24 as a colorless solid (11.36 g/yield: 40%).

Chemical Formula 24

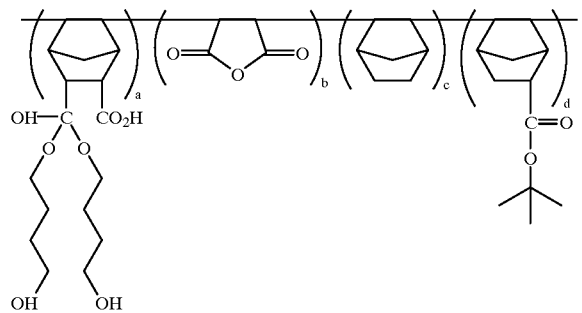

EXAMPLE 19

Synthesis of poly(5-norbornene-2-carboxylic acid-3-[1,1-di(5-hydroxypentyloxy)]methanol/maleic anhydride/norbornene/tert-butyl-5-norbornene-2-carboxylate)

The procedure of Example 16 was repeated but using 5-norbornene-2-carboxylic acid-3-[1,1-di(5-hydroxypentyloxy)]methanol instead of 5-norbornene-2-carboxylic acid-3-[1,1-di(2-hydroxyethoxy)]methanol, to obtain the compound represented by following Chemical Formula 25 as a colorless solid (11.7 g/yield: 41%).

Chemical Formula 25

EXAMPLE 20

Synthesis of poly(5-norbornene-2-carboxylic acid-3-[1,1-di(2-hydroxyethoxyethoxy)]methanol/maleic anhydride/norbornene/tert-butyl-5-norbornene-2-carboxylate)

The procedure of Example 16 was repeated but using 5-norbornene-2-carboxylic acid-3-[1,1-di(2-hydroxyethoxyethoxy)]methanol instead of 5-norbornene-2-carboxylic acid-3-[1,1-di(2-hydroxyethoxy)]methanol, to obtain the compound represented by following Chemical Formula 26 as a colorless solid (27.6 g/yield: 45%).

Chemical Formula 26

EXAMPLE 21

Synthesis of poly{oxabicyclo[2.2.1]hept-5-ene-2-carboxylic acid-3-[1,1-di(2-hydroxyethoxy)]methanol/maleic anhydride/norbornene/tert-butyl-5-norbornene-2-carboxylate}

The procedure of Example 16 was repeated but using oxabicyclo[2.2.1]hept-5-ene-2-carboxylic acid-3-[1,1-di(2-hydroxyethoxy)]methanol instead of 5-norbornene-2-carboxylic acid-3-[1,1-di(2-hydroxyethoxy)]methanol, to obtain the compound represented by following Chemical Formula 27 as a colorless solid (11.7 g/yield: 43%).

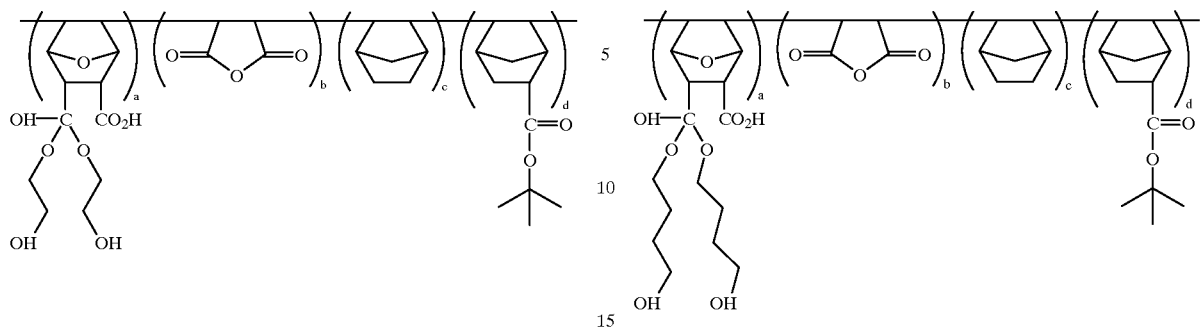

Chemical Formula 27 / Chemical Formula 29

EXAMPLE 22

Synthesis of poly{oxabicyclo[2.2.1]hept-5-ene-2-carboxylic -acid-3-[1,1-di(3-hydroxypropyloxy)]methanol/maleic anhydride/norbornene/tert-butyl-5-norbornene-2-carboxylate}

The procedure of Example 16 was repeated but using oxabicyclo[2.2.1]hept-5-ene-2-carboxylic acid-3-[1,1-di(3-hydroxypropyloxy)]methanol instead of 5-norbornene-2-carboxylic acid-3-[1,1-di(2-hydroxyethoxy)]methanol, to obtain the compound represented by following Chemical Formula 28 as a colorless solid (11.7 g/yield: 43%).

EXAMPLE 24

Synthesis of poly{oxabicyclo[2.2.1]hept-5-ene-2-carboxylic acid-3-[1,1-di(5-hydroxypentyloxy)]methanol/maleic anhydride/norbornene/tert-butyl-5-norbornene-2-carboxylate}

The procedure of Example 16 was repeated but using oxabicyclo[2.2.1]hept-5-ene-2-carboxylic acid-3-[1,1-di(5-hydroxypentyloxy)]methanol instead of 5-norbornene-2-carboxylic acid-3-[1,1-di(2-hydroxyethoxy)]methanol, to obtain the compound represented by following Chemical Formula 30 as a colorless solid (10.9 g/yield: 39%).

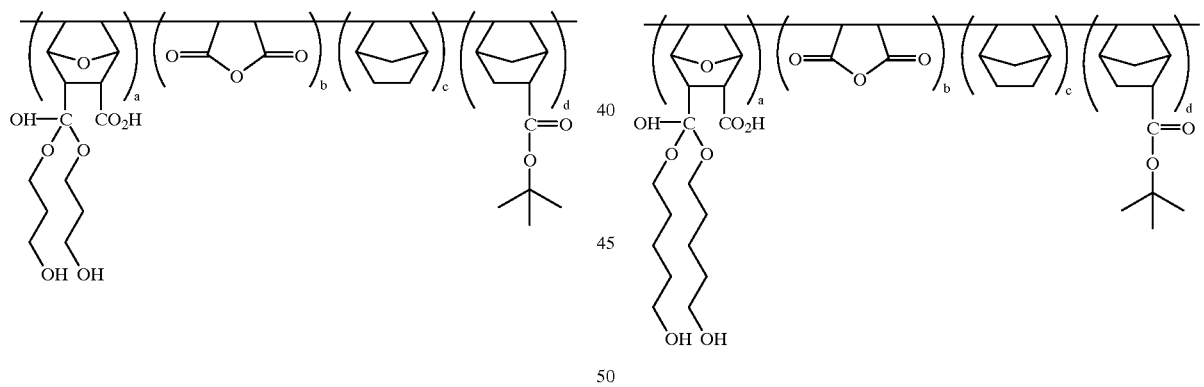

Chemical Formula 28 / Chemical Formula 30

EXAMPLE 23

Synthesis of poly{oxabicyclo[2.2.1]hept-5-ene-2-carboxylic acid-3-[1,1-di(4-hydroxybutyloxy)]methanol/maleic anhydride/norbornene/tert-butyl-5-norbornene-2-carboxylate}

The procedure of Example 16 was repeated but using oxabicyclo[2.2.1]hept-5-ene-2-carboxylic acid-3-[1,1-di(4-hydroxybutyloxy)]methanol instead of 5-norbornene-2-carboxylic acid-3-[1,1-di(2-hydroxyethoxy)]methanol, to obtain the compound represented by following Chemical Formula 29 as a colorless solid (10.9 g/yield: 39%).

EXAMPLE 25

Synthesis of poly{oxabicyclo[2.2.1]hept-5-ene-2-carboxylic acid-3-[1,1-di(2-hydroxyethoxyethoxy)]methanol/maleic anhydride/norbornene/tert-butyl-5-norbornene-2-carboxylate}

The procedure of Example 16 was repeated but using oxabicyclo[2.2.1]hept-5-ene-2-carboxylic acid-3-[1,1-di(2-hydroxyethoxyethoxy)]methanol instead of 5-norbornene-2-carboxylic acid-3-[1,1-di(2-hydroxyethoxy)]methanol, to obtain the compound represented by following Chemical Formula 31 as a colorless solid (10.9 g/yield: 39%).

Chemical Formula 31

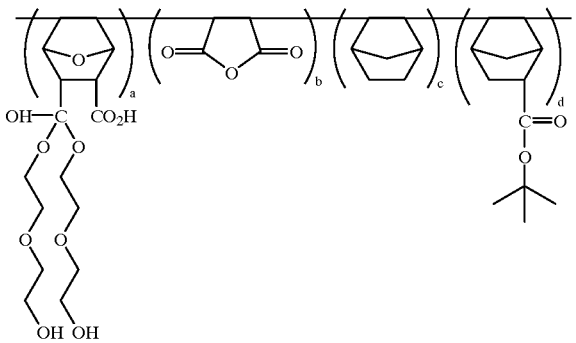

In the above polymers represented by Chemical Formula 22–31, the ratio a:b:c:d=1–20 mol %: 50 mol %: 1–30 mol %: 10–40 mol %.

EXAMPLE 26

Synthesis of poly(5-norbornene-2-carboxylic acid-3-[1,1-di(2-hydroxyethoxy)]methanol/maleic anhydride/t-butyl-5-norbornene-2-carboxylate)

A 0.2 mole 5-norbornene-2-carboxylic acid-3-[1,1-di(2-hydroxyethoxy)]methanol (the first monomer), 0.8 mole t-butyl-5-norbornene-2-carboxylate (the second monomer) and 1.0 mole maleic anhydride (the third monomer) were dissolved in 30 ml of tetrahydrofuran. The resulting solution was mixed with 0.5 to 10 g of AIBN (polymerization initiator). The mixture was reacted at 60 to 70° C. under an atmosphere of argon for 4 to 24 hours.

After completion of the reaction, the resulting polymer was precipitated in ethyl ether or hexane, and dried to obtain poly(5-norbornene-2-carboxylic acid-3-[1,1-di(2-hydroxyethoxy)]methanol/maleic anhydride/t-butyl-5-norbornene-2-carboxylate) (yield: 37%).

EXAMPLE 27

Synthesis of poly(mono-3-[1,1-di(2-hydroxyethoxy)-1-hydroxy]methyl bicyclo[2.2.2]oct-5-en-2,3-dicarboxylate/maleic anhydride/t-butyl-5-norbornene-2-carboxylate)

The same method as described in Example 26 was carried out, but replacing 0.2 mole 5-norbornene-2-carboxylic acid-3-[1,1-di(2-hydroxyethoxy)]methanol with 0.2 mole mono-3-[1,1-di(2-hydroxyethoxy)-1-hydroxy]methyl bicyclo[2.2.2]oct-5-en-2,3-dicarboxylate (the first monomer), to afford poly(mono-3-[1,1-di(2-hydroxyethoxy)-1-hydroxy]methyl bicyclo[2.2.2]oct-5-en-2,3-dicarboxylate/maleic anhydride/t-butyl-5-norbornene-2-carboxylate) (yield: 36%).

EXAMPLE 28

The copolymer represented by Chemical Formula 22, obtained from Example 16 (10 g) and triphenylsulfonium triflate (0.12 g) as a photoacid generator were dissolved in ethyl 3-ethoxypropionate solvent (60 g), and the resultant mixture was filtered through a 0.10 µm filter to prepare a photoresist solution. The photoresist solution thus prepared was spin-coated on a silicon wafer, and soft-baked at 110° C. for 90 seconds. After baking, the photoresist was exposed to light by using an ArF laser exposer, and then post-baked at 110° C. for 90 seconds. When the post-baking was completed, it was developed in 2.38 wt % aqueous TMAH (tetramethylammonium hydroxide) solution for 40 seconds, to obtain a 0.11 µm L/S pattern.

EXAMPLE 29

The procedure according to Example 28 was repeated but using the copolymer represented by Chemical Formula 23, obtained from Example 17, instead of the copolymer of Chemical Formula 22, to prepare a photoresist composition. By employing the composition, a 0.12 µm L/S pattern was obtained.

EXAMPLE 30

The procedure according to Example 28 was repeated but using the copolymer represented by Chemical Formula 24, obtained from Example 18, instead of the copolymer of Chemical Formula 22, to prepare a photoresist composition. By employing the composition, a 0.12 µm L/S pattern was obtained.

EXAMPLE 31

The procedure according to Example 28 was repeated but using the copolymer represented by Chemical Formula 25, obtained from Example 19, instead of the copolymer of Chemical Formula 22, to prepare a photoresist composition. By employing the composition, a 0.13 µm L/S pattern was obtained.

EXAMPLE 32

The procedure according to Example 28 was repeated but using the copolymer represented by Chemical Formula 26, obtained from Example 20, instead of the copolymer of Chemical Formula 22, to prepare a photoresist composition. By employing the composition, a 0.13 µm L/S pattern was obtained.

EXAMPLE 33

The procedure according to Example 28 was repeated but using the copolymer represented by Chemical Formula 27, obtained from Example 21, instead of the copolymer of Chemical Formula 22, to prepare a photoresist composition. By employing the composition, a 0.13 µm L/S pattern was obtained.

EXAMPLE 34

The procedure according to Example 28 was repeated but using the copolymer represented by Chemical Formula 28, obtained from Example 22, instead of the copolymer of Chemical Formula 22, to prepare a photoresist composition. By employing the composition, a 0.12 µm L/S pattern was obtained.

EXAMPLE 35

The procedure according to Example 28 was repeated but using the copolymer represented by Chemical Formula 29, obtained from Example 23, instead of the copolymer of Chemical Formula 22, to prepare a photoresist composition. By employing the composition, a 0.12 µm L/S pattern was obtained.

EXAMPLE 36

The procedure according to Example 28 was repeated but using the copolymer represented by Chemical Formula 30, obtained from Example 24, instead of the copolymer of Chemical Formula 22, to prepare a photoresist composition. By employing the composition, a 0.13 µm L/S pattern was obtained.

EXAMPLE 37

The procedure according to Example 28 was repeated but using the copolymer represented by Chemical Formula 31, obtained from Example 25, instead of the copolymer of Chemical Formula 22, to prepare a photoresist composition. By employing the composition, a 0.13 µm L/S pattern was obtained.

EXAMPLE 38

The procedure according to Example 28 was repeated but using the copolymer obtained from Example 26, instead of the copolymer of Chemical Formula 22, to prepare a photoresist composition. By employing the composition, a 0.13 µm L/S pattern was obtained.

EXAMPLE 39

The procedure according to Example 28 was repeated but using the copolymer obtained from Example 27, instead of the copolymer of Chemical Formula 22, to prepare a photoresist composition. By employing the composition, a 0.13 µm L/S pattern was obtained.

In the processes for pattern formation described above, KrF, E-beam, EUV (extreme ultraviolet) or ion beam may be used instead of an ArF light source, as an exposing device. The irradiated energy is preferably 0.1 to 100 mJ/cm².

The soft-baking and post-baking are preferably carried out at a temperature of 70 to 200° C.

What is claimed is:

1. A photoresist monomer represented by following Chemical Formula 1:

<Chemical Formula 1>

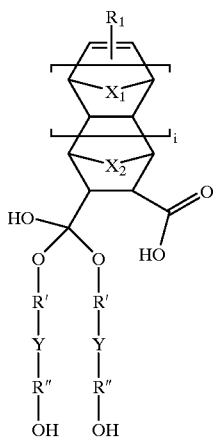

wherein, $X_1$ and $X_2$ individually represent $CH_2$, $CH_2CH_2$, oxygen or sulfur; Y represents $CH_2$ or oxygen; $R_1$ represents H or $CH_3$, R' and R" individually represent substituted or non-substituted ($C_0$–$C_3$) alkyl; and i is an integer from 0 to 3.

2. A photoresist monomer according to claim 1, which is selected from the group consisting of 5-norbornene-2-carboxylic acid-3-[1,1-di(2-hydroxyethoxy)]methanol, 5-norbornene-2-carboxylic acid-3-[1,1-di(3-hydroxypropyloxy)methanol, 5-norbornene-2-carboxylic acid-3-[1,1-di(4-hydroxybutyloxy)]methanol, 5-norbornene-2-carboxylic acid-3-[1,1-di(5-hydroxypentyloxy)]methanol, 5-norbornene-2-carboxylic acid-3-[1,1-di(2-hydroxyethoxyethoxy)]methanol, methyl 5-norbornene-2-carboxylic acid-3-[1,1-di(2-hydroxyethoxy)]methanol, methyl 5-norbornene-2-carboxylic acid-3-[1,1-di(2-hydroxypropyloxy)]methanol, methyl 5-norbornene-2-carboxylic acid-3-[1,1-di(4-hydroxybutyloxy)]methanol, 5-norbornene-2-carboxylic acid-3-[1,1-di(5-hydroxypentyloxy)]methanol, methyl 5-norbornene-2-carboxylic acid-3-[1,1-di(2-hydroxyethoxyethoxy)]methanol, oxabicyclob[2.2.1]hept-5-ene-2-carboxylic acid-3-[1,1-di(2-hydroxyethoxy)]methanol, oxabicyclo[2.2.1]-hept-5-ene-2-carboxylic acid-3-[1,1-di(3-hydroxypropyloxy)methanol, oxabicyclo[2.2.1]-hept-5-ene-2-carboxylic acid-3-[1,1-di(4-hydroxybutyloxy)]methanol, oxabicyclo[2.2.1]-hept-5-ene-2-carboxylic acid-3-[1,1 -di(5-hydroxypentyloxy)]methanol and oxabicyclo[2.2.1]-hept-5-ene-2-carboxylic acid-3-[1,1-di(2-hydroxyethoxyethoxy)]methanol.

3. A process for preparing the photoresist monomer of claim 1; which comprises the steps of (a) dissolving the compound represented by following Chemical Formula 2 in a conventional organic solvent:

<Chemical Formula 2>

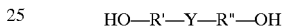

HO—R'—Y—R"—OH wherein Y represents $CH_2$ or oxygen; and R' and R" individually represent substituted or non-substituted ($C_0$–$C_3$) alkyl (b) reacting therewith in the presence of acid catalyst, or under basic conditions, a compound represented by following Chemical Formula 3:

Chemical Formula 3

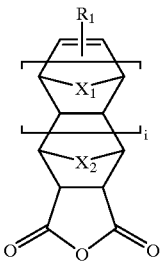

wherein $X_1$ and $X_2$ individually represent $CH_2$, $CH_2CH_2$, oxygen or sulfur; $R_1$ represents H or $CH_3$; and i is an integer from 0 to 3

(c) distilling off the organic solvent therefrom; (d) neutralizing and extracting the resultant solution of step (c); and (e) recrystallizing the extract from an organic solvent.

4. A process according to claim 3, wherein the compound represented by Chemical Formula 2 is selected from the group consisting of ethylene glycol, 1,3-propanediol, 1,4-butanediol, 1,5-pentanediol and diethylene glycol.

5. A process according to claim 3, wherein the compound represented by Chemical Formula 3 is 5-norbornene-2,3-dicarboxylic anhydride or exo-3,6-epoxy-1,2,3,6-tetrahydrophthalic anhydride.

6. A process according to claim 3, wherein the compound of Chemical Formula 2 is used in an amount of 2 molar equivalents or more of the compound of Chemical Formula 3.

7. A process according to claim 3, wherein the organic solvent of step (a) is selected from the group consisting of tetrahydrofuran, dimethylformamide, dioxane, benzene and toluene.

8. A process according to claim 3, wherein the basic condition is established by adding a substance selected from the group consisting of NaH, KH, $CaH_2$, $Na_2CO_3$, $K_2CO_3$ and LDA (lithium diisopropylamide) to the solution, and the acid catalyst is selected from the group consisting of sulfuric acid, nitric acid and acetic acid.

9. A process according to claim 3, wherein said extracting step of (d) is performed using an extracting solvent and said extracting solvent is removed by dehydration and evaporation before said step (e).

10. A process according to claim 9, wherein the drying step is carried out by using magnesium sulfate ($MgSO_4$) or sodium sulfate ($Na_2SO_4$).

11. A photoresist copolymer comprising a monomer represented by following Chemical Formula 1:

<Chemical Formula 1>

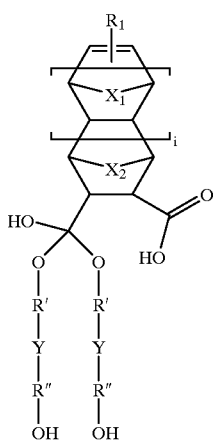

wherein, $X_1$ and $X_2$ individually represent $CH_2$, $CH_2CH_2$, oxygen or sulfur; Y represents $CH_2$ or oxygen; $R_1$ represents H or $CH_3$, R' and R'' individually represent substituted or non-substituted($C_0$–$C_3$)alkyl, and i is an integer from 0 to 3.

12. A photoresist copolymer according to claim 11, which further comprises a compound represented by following Chemical Formula 4 as a second comonomer:

Chemical Formula 4

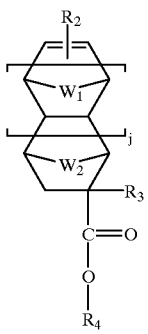

wherein $W_1$ and $W_2$ individually represent $CH_2$, $CH_2CH_2$ or oxygen; $R_2$ and $R_3$ individually represent H or $CH_3$; $R_4$ is an acid labile protective group; and j is an integer from 0 to 4.

13. A photoresist copolymer according to claim 11 or 12, which further comprises maleic anhydride as an additional comonomer.

14. A photoresist copolymer according to claim 13, which further comprises a compound represented by following Chemical Formula 5 as an additional comonomer:

Chemical Formula 5

wherein Z represents $CH_2$, $CH_2CH_2$ or oxygen.

15. A copolymer according to claim 14, wherein a maleic anhydride unit is present in the polymer after each of the other monomers.

16. A photoresist copolymer according to claim 11, which is represented by the following Chemical Formula 6:

Chemical Formula 6

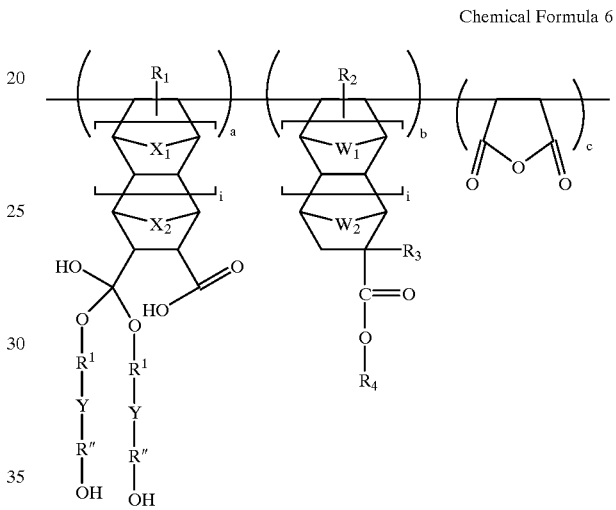

wherein $X_1$ and $X_2$ individually represent $CH_2$, $CH_2CH_2$, oxygen or sulfur; Y represents $CH_2$ or oxygen; $W_1$ and $W_2$ individually represent $CH_2$, $CH_2CH_2$ or oxygen; $R_1$, $R_2$ and $R_3$ individually represent H or $CH_3$; $R_4$ represents an acid labile protective group; R' and R'' individually represent substituted or non-substituted ($C_0$–$C_3$)alkyl; i and j individually represent integers from 0 to 3; and a, b, c and d represent the number of repeating units derived from each monomer.

17. A photoresist copolymer according to claim 12 or 16, wherein $R_4$ is tert-butyl, 2-tetrahydrofuranyl or 2-tetrahydropyranyl.

18. A photoresist copolymer according to claim 16, wherein the molecular weight of the copolymer represented by Chemical Formula 6 is 3,000 to 100,000.

19. A copolymer according to claim 16, wherein the ratio, a:b:c:d is 1–20 mol %: 10–49 mol %: 50 mol %: 1–30 mol %.

20. A photoresist copolymer according to claim 11, which is selected from the group consisting of poly(5-norbornene-2-carboxylic acid-3-[1,1-di(2-hydroxyethoxy)]methanol/ maleic anhydride/norbornene/tert-butyl-5-norbornene-2-carboxylate); poly(5-norbornene-2-carboxylic acid-3-[1,1-di(3-hydroxypropyloxy)]methanol/maleic anhydride/ norbornene/tert-butyl-5-norbornene-2-carboxylate); poly(5-norbornene-2-carboxylic acid-3-[1,1-di(4-hydroxybutyloxy)]methanol/maleic anhydride/norbornene/ tert-butyl-5-norbornene-2 -carboxylate); poly(5-norbornene-2-carboxylic acid-3-[1,1-di(5-hydroxypentyloxy)]methanol/maleic anhydride/norbornene/ tert-butyl-5-norbornene-2-carboxylate); poly(5-norbornene- 2-carboxylic acid-3-[1,1-di(2-hydroxyethoxyethoxy)] methanol/maleic anhydride/norbornene/tert-butyl-5-norbornene-2-carboxylate); poly{oxabicyclo[2.2.1]hept-5-ene-2-carboxylic acid-3-[1,1-di(2-hydroxyethoxy)] methanol/maleic anhydride/norbornene/tert-butyl-5-norbornene-2-carboxylate}; poly{oxabicyclo[2.2.1]hept-5-ene-2-carboxylic acid-3-[1,1-di(3-hydroxypropyloxy)] methanol/maleic anhydride/norbornene/tert-butyl-5-norbornene-2-carboxylate}; poly {oxabicyclo[2.2.1]hept-5-ene-2-carboxylic acid-3-[1,1-di(4-hydroxybutyloxy)] methanol/maleic anhydride/norbornene/tert-butyl-5-norbornene-2-carboxylate}; poly{oxabicyclo[2.2.1]hept-5-ene-2-carboxylic acid-3-[1,1-di(5-hydroxypentyloxy)] methanol/maleic anhydride/norbornene/tert-butyl-5-norbornene-2-carboxylate}; poly {oxabicyclo[2.2.1]hept-5-ene-2-carboxylic acid-3-[1,1-di(2-hydroxyethoxyethoxy)] methanol/maleic anhydride/norbornene/tert-butyl-5-norbornene-2-carboxylate}; poly(5-norbornene-2-carboxylic acid-3-[1,1-di(2-hydroxyethoxy)]methanol/ maleic anhydride/tert-butyl-5-norbornene-2-carboxylate); poly {mono-3-[1,1-di(2-hydroxyethoxy)-1-hydroxy]methyl bicyclo[2.2.2]oct-5-ene-2,3-dicarboxylate/maleic anhydride/tert-butyl bicyclo[2.2.2]oct-5-endo-2-carboxylate}; poly(5-norbornene-2-carboxylic acid-3-[1,1-di(4-hydroxybutyloxy)]methanol/maleic anhydride/tert-butyl-5-norbornene-2-carboxylate); and poly(5-norbornene-2-carboxylic acid-3-[1,1-di(4-hydroxybutyloxy)]methanol/ maleic anhydride/tert-butyl bicyclo[2.2.2]oct-5-endo-2-carboxylate).

21. A process for preparing a photoresist copolymer, which comprises the steps of (a) dissolving (i) a first monomer represented by following Chemical Formula 1:

<Chemical Formula 1>

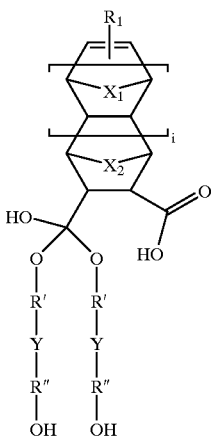

wherein, $X_1$ and $X_2$ individually represent $CH_2$, $CH_2CH_2$, oxygen or sulfur; Y represents $CH_2$ or oxygen; $R_1$ represents H or $CH_3$, R' and R" individually represent substituted or non-substituted($C_0$–$C_3$)alkyl, and i is an integer from 0 to 3;

and (ii) one or more compounds selected from the group consisting of maleic anhydride, monomers of Chemical Formula 4:

Chemical Formula 4

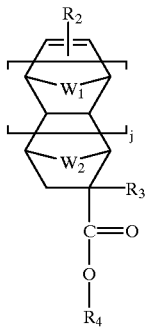

wherein $W_1$ and $W_2$ individually represent $CH_2$, $CH_2CH_2$ or oxygen; $R_2$ and $R_3$ individually represent H or $CH_3$; $R_4$ is an acid labile protective group; and j is an integer from 0 to 3; and monomers of Chemical Formula 5:

Chemical Formula 5

wherein Z represents $CH_2$, $CH_2CH_2$ or oxygen, in organic solvent in the presence of a polymerization initiator to carry out a polymerization reaction; and (b) pouring the resultant solution into a solvent for crystallization to obtain the copolymer.

22. A process according to claim 21, wherein the organic solvent for polymerization is selected from the group consisting of tetrahydrofuran, dimethylformamide, dimethyl sulfoxide, dioxane, cyclohexanone, methyl ethyl ketone, benzene, toluene and xylene.

23. A process according to claim 21, wherein the solvent for crystallization is selected from the group consisting of diethyl ether, methanol, ethanol, isopropanol and petroleum ether.

24. A process according to claim 21, wherein the polymerization initiator is selected from the group consisting of 2,2-azobisisobutyronitile (AIBN), acetyl peroxide, lauryl peroxide, benzoyl peroxide, tert-butyl peroxide and t-butyl peracetate.

25. A photoresist composition which comprises (i) a photoresist copolymer according to claim 11, (ii) a photoacid generator and (iii) an organic solvent.

26. A photoresist composition according to claim 25, wherein the photoacid generator is one or more compound (s) selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate.

27. A photoresist composition according to claim 25, wherein the photoacid generator is used in an amount of 0.05 to 10% by weight of the copolymer employed.

28. A photoresist composition according to claim 25, wherein the organic solvent is selected from the group consisting of cyclohexanone, methyl 3-methoxypropionate, ethyl 3-ethoxypropionate and propylene glycol methyl ether acetate.

29. A photoresist composition according to claim 25, wherein the organic solvent is used in an amount of 200 to 1000% by weight of the copolymer employed.

30. A process for forming a photoresist pattern, which comprises the steps of (a) coating a photoresist composition of claim 25 on a substrate of a semiconductor element to form a photoresist film; (b) exposing the photoresist film to light; and (c) developing the photoresist film.

31. A process for forming a photoresist pattern according to claim 30, which further comprises baking step(s) before and/or after step (b).

32. A process for forming a photoresist pattern according to claim 31, wherein the baking is performed at 70–200° C.

33. A process for forming a photoresist pattern according to claim 30, wherein step (b) is carried out by using ArF, KrF, DUV, E-beam, EUV, VUV (Vacuum Ultra Violet) or X-ray light source.

34. A process for forming a photoresist pattern according to claim 30, wherein step (b) is carried out by irradiating 0.1 to 100 mJ/cm$^2$ of light-exposure energy.

35. A semiconductor element manufactured by employing the process according to claim 30.

* * * * *

UNITED STATES PATENT AND TRADEMARK OFFICE
CERTIFICATE OF CORRECTION

PATENT NO. : 6,235,447 B1
DATED : May 22, 2001
INVENTOR(S) : Geun Su Lee; Cha Won Koh; Jae Chang Jung; Min Ho Jung; Ki Ho Baik It is certified that error appears in the above-identified patent and that said Letters Patent is hereby corrected as shown below:

<u>Column 12,</u>
Chemical Formula 17, the "$CH_3$" should read -- $CH_2$ --

Signed and Sealed this

Thirteenth Day of November, 2001

Attest:

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO.    : 6,235,447 B1
DATED         : May 22, 2001
INVENTOR(S)   : Geun Su Lee; Cha Won Koh; Jae Chang Jung; Min Ho Jung; Ki Ho Baik It is certified that error appears in the above-identified patent and that said Letters Patent is hereby corrected as shown below:

Title page,
Under FOREIGN APPLICATION PRIORITY DATA, reading "Feb. 4, 1999 (JP)" should read -- Feb. 4, 1999 (KR) --.

Column 1,
Line 12, reading "light sources such as KrF (249 mm) and ArF(193um); EUV;" should read -- light sources such as KrF (249 nm) and ArF(193nm); EUV; --.

Column 9,
Line 64, reading "1,4-butanediol instead –of ethylene glycol as a starting" should read -- 1,4-butanediol instead of ethylene glycol as a starting --.

Column 13,
Line 46, reading "acid-3-[1,1-di(5-hydroxyethoxyethoxy)]methanol" should read -- acid-3-[1,1-di(5-hydroxypentyloxy)]methanol --.

Column 17,
Line 23, reading "carboxylic -acid-3-[1,1di(3-hydroxypropyloxy)]methanol/" should read -- carboxylic acid-3-[1,1-di(3-hydroxypropyloxy)]methanol/ --.

Column 22, claim 2,
Line 6, reading "carboxylic acid-3-[1,1-di(2-hydroxypropyloxy)]methanol" should read -- carboxylic acid-3-[1,1-di(3-hydroxypropyloxy)]methanol --.

Signed and Sealed this

Second Day of April, 2002

*Attest:*

JAMES E. ROGAN
*Attesting Officer*        *Director of the United States Patent and Trademark Office*